(12) United States Patent
Kaneko

(10) Patent No.: US 9,110,043 B2
(45) Date of Patent: Aug. 18, 2015

(54) CUVETTE SUPPLYING DEVICE AND SPECIMEN ANALYZER

(75) Inventor: Shuhei Kaneko, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 155 days.

(21) Appl. No.: 13/337,574

(22) Filed: Dec. 27, 2011

(65) Prior Publication Data

US 2012/0171078 A1    Jul. 5, 2012

(30) Foreign Application Priority Data

Dec. 29, 2010  (JP) ................. 2010-294565

(51) Int. Cl.
| | |
|---|---|
| *G01N 35/04* | (2006.01) |
| *B65G 47/14* | (2006.01) |
| *B65G 47/18* | (2006.01) |
| *G01N 35/02* | (2006.01) |
| *G01N 35/00* | (2006.01) |

(52) U.S. Cl.
CPC ............ *G01N 35/04* (2013.01); *B65G 47/1471* (2013.01); *G01N 35/025* (2013.01); *G01N 35/021* (2013.01); *G01N 35/026* (2013.01); *G01N 2035/00306* (2013.01); *G01N 2035/0446* (2013.01); *G01N 2035/0465* (2013.01); *G01N 2035/0491* (2013.01)

(58) Field of Classification Search
CPC ............................ G01N 35/04; B65G 47/1471
See application file for complete search history.

(56) References Cited

U.S. PATENT DOCUMENTS

| | | | | |
|---|---|---|---|---|
| 3,276,566 | A * | 10/1966 | Raasch .......................... | 198/395 |
| 6,325,129 | B1 * | 12/2001 | Wright et al. .................. | 156/538 |
| 6,409,007 | B1 * | 6/2002 | Malon ............................ | 198/396 |
| 7,931,861 | B2 | 4/2011 | Kitagawa | |
| 2007/0269342 | A1 * | 11/2007 | Kitagawa ........................ | 422/64 |

FOREIGN PATENT DOCUMENTS

| | | |
|---|---|---|
| EP | 0181792 | 5/1986 |
| FR | 1452872 | 4/1966 |
| JP | 2003-083999 A | 3/2003 |

* cited by examiner

*Primary Examiner* — P. Kathryn Wright
(74) *Attorney, Agent, or Firm* — Brinks Gilson & Lione

(57) ABSTRACT

A cuvette supplying device is disclosed. The cuvette supplying device comprises: a cuvette storage for storing cuvettes; a carrier, provided inside the cuvette storage, for carrying the cuvettes in the cuvette storage outside the cuvette storage; a conveyor for conveying the cuvettes existing at the bottom of the cuvette storage towards the carrier; and an arranging section for arranging the cuvettes carried outside the cuvette storage by the carrier at a predetermined position. The specimen analyzer comprising the cuvette supplying device is also disclosed.

18 Claims, 13 Drawing Sheets

CUVETTE SUPPLYING DEVICE AND SPECIMEN ANALYZER

RELATED APPLICATIONS

This application claims priority under 35 U.S.C. §119 to Japanese Patent Application No. 2010-294565 filed on Dec. 29, 2010, the entire content of which is hereby incorporated by reference.

BACKGROUND OF THE INVENTION

1. Field of the Invention

The present invention relates to a cuvette supplying device and a specimen analyzer.

2. Description of the Related Art

A specimen analyzer equipped with a cuvette supplying device for supplying a translucent container (cuvette) used for the optical detection of a specimen is conventionally known (see e.g., U.S. Pat. No. 7,931,861).

As shown in FIG. 12, the cuvette supplying device includes a first accumulation unit 401 for accumulating a cuvette inserted by a user, an annular belt 403 for carrying out a cuvette 402 stored in the first accumulation unit 401, and a second accumulation unit 404 for accumulating the cuvette 402 carried out by the annular belt 403.

The cuvette 402 accumulated in the first accumulation unit 401 is scooped up by a holding plate 405 attached to the annular belt 403 with the rotation of the annular belt 403, and carried out to the second accumulation unit 404.

The cuvette 402 carried out to the second accumulation unit 404 is passed through a predetermined passage one at a time and aligned on a transportation rail 406, and is rotationally transferred by a rotation transfer unit 407 arranged at the tip of the transportation rail 406. The rotationally transferred cuvette 402 is supplied to a dispensing table by a supplying catcher unit (not shown).

SUMMARY OF THE INVENTION

A first aspect of the present invention is a cuvette supplying device comprising: a cuvette storage for storing cuvettes; a carrier, provided inside the cuvette storage, for carrying the cuvettes in the cuvette storage outside the cuvette storage; a conveyor for conveying the cuvettes existing at the bottom of the cuvette storage towards the carrier; and an arranging section for arranging the cuvettes carried outside the cuvette storage by the carrier at a predetermined position.

A second aspect of the present invention is a specimen analyzer comprising the device according to the first aspect, an optical detector for optically interrogating a specimen accommodated in a cuvette; and a container transporter for transporting the cuvette arranged at the predetermined position to the optical detector.

DETAILED DESCRIPTION OF THE PREFERRED EMBODIMENTS

Embodiments of the present invention will be hereinafter described based on the drawings.

[1. Overall Configuration of Specimen Analyzer 1]

A specimen analyzer 1 according to the present embodiment is an apparatus for analyzing the amount or degree of activity of a specific substance related to coagulation and fibrolytic function of the blood by optically measuring the same.

Figure 1:
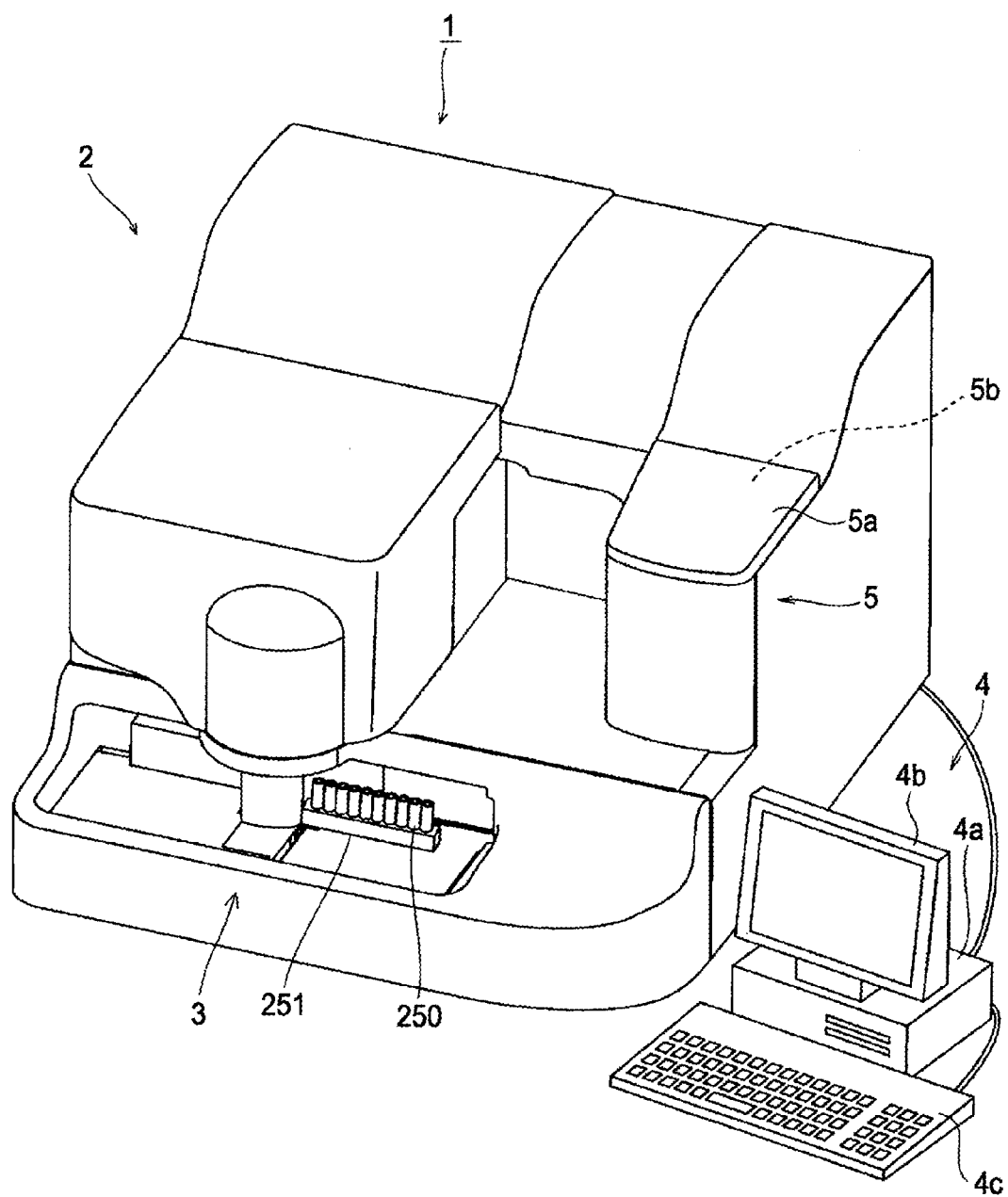
FIG. 1 is a perspective view showing an outer appearance of a specimen analyzer.

As shown in FIG. 1, the specimen analyzer 1 includes a measurement mechanism section 2, a transport mechanism section 3 arranged on a front face side of the measurement mechanism section 2, and a control device 4 electrically connected to the measurement mechanism section 2. The measurement mechanism section 2 includes an insertion unit 5 for the user to insert a cuvette (specimen container) 200 or a container of a sample when performing a measurement. The insertion unit 5 has an opening that opens to an upper side, which opening is an insertion port 5b of the cuvette 200. A lid 5a for opening and closing the insertion port 5b is also arranged. The cuvette 200 is inserted to an cuvette storage 9 (see FIG. 4) of a cuvette supply mechanism section 6, to be described later, through the insertion port 5b.

[2. Configuration of Control Device 4]

The control device 4 includes a personal computer (PC), and includes a control unit 4a, a display unit 4b and a keyboard 4c. The control unit 4a has a function of transmitting an operation start signal of the measurement mechanism section 2 to a control unit (not shown) of the measurement mechanism section 2, and analysis processing optical information of a sample obtained in the measurement mechanism section 2. The control unit 4a is made up of CPU, ROM, RAM, or the like. The display unit 4b can display various types of information, and displays analysis result etc. obtained by the control unit 4a, the notification information to the user, and the like.

[3. Configuration of Transport Mechanism Section 3]

Figure 2:
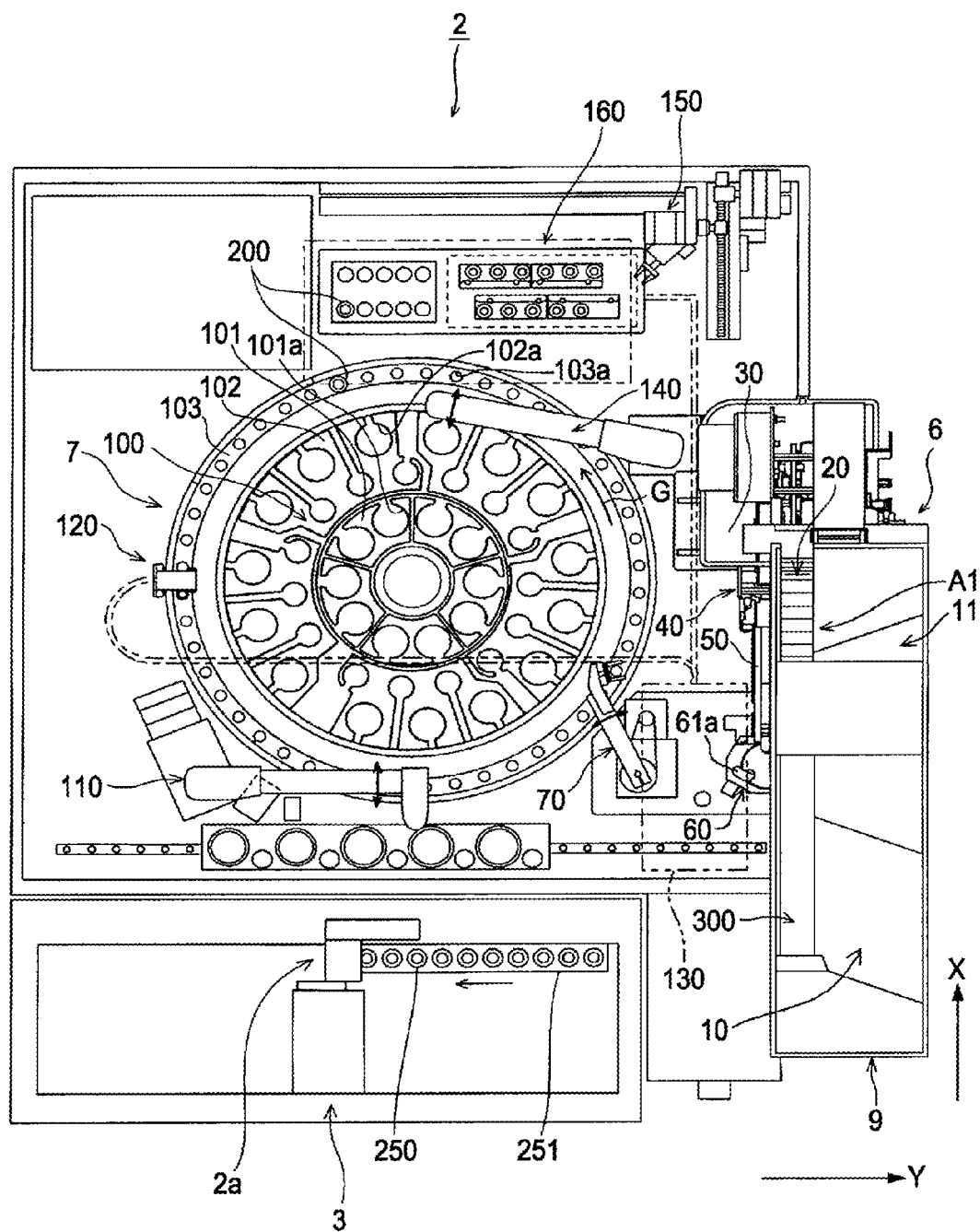
FIG. 2 is an internal plan view of the specimen analyzer.

As shown in FIG. 1 and FIG. 2, the transport mechanism section 3 has a function of transporting a rack 251 mounted with a plurality of (ten in the present embodiment) test tubes 250 accommodating a sample to an aspirating position 2a (see FIG. 2) of the measurement mechanism section 2 to supply the sample to the measurement mechanism section 2.

[4. Configuration of Measurement Mechanism Section 2]

The measurement mechanism section 2 performs optical measurement on the sample supplied from the transport mechanism section 3 to acquire optical information about the supplied sample. In the present embodiment, the optical measurement is performed on the sample dispensed into the cuvette 200 of the measurement mechanism section 2 from the test tube 250 mounted on the rack 251 of the transport mechanism section 3. The measurement mechanism section 2 includes a cuvette supply mechanism section 6 and an analysis mechanism section (optical detector) 7.

[4.1 Analysis Mechanism Section 7]

The analysis mechanism section 7 includes a rotation transport unit 100, a sample dispensing arm 110, a first optical information acquiring unit 120, a lamp unit 130, a reagent dispensing arm 140, a cuvette moving unit 150, and a second optical information acquiring unit 160.

The rotation transport unit 100 transports the cuvette 200 supplied from the cuvette supply mechanism section 6 and a reagent container (not shown) accommodating a reagent to be added to the sample in the cuvette 200 in the rotation direction. The rotation transport unit 100 is configured by a circular reagent table 101, a circular ring shaped reagent table 102 arranged on an outer side of the reagent table 101, and a circular ring shaped dispensing table 103 arranged on an outer side of the reagent table 102. The dispensing table 103, the reagent table 101, and the reagent table 102 are independently rotatable.

The reagent tables 101 and 102 respectively have a plurality of holes 101a and 102a arranged with a predetermined interval along a circumferential direction. The holes 101a and 102 are for mounting a plurality of reagent containers (not shown) accommodating various reagents to be added when preparing a measurement specimen from the sample. The dispensing table 103 includes a plurality of cylindrical holders 103a arranged with a predetermined interval along the circumferential direction. The holder 103a holds the cuvette 200 supplied from the cuvette supply mechanism section 6. The sample accommodated in the test tube 250 of the transport mechanism section 3 is dispensed to the cuvette 200 held in the holder 103a in the dispensing process.

The sample dispensing arm 110 aspirates the sample accommodated in the test tube 250 transported to the aspirating position 2a by the transport mechanism section 3 and dispenses the aspirated sample into the cuvette 200 transferred to the rotation transport unit 100.

The first optical information acquiring unit 120 acquires optical information from the sample to measure the presence/absence and the concentration of an interfering substance in the sample of before the reagent is added. The first optical information acquiring unit 120 acquires optical information (information by transmitted light of sample) from the sample in the cuvette 200 held in the holder 103a of the dispensing table 103.

The first optical information acquiring unit 120 is electrically connected to the control unit 4a of the control device 4, where data (optical information) acquired by the first optical information acquiring unit 120 is transmitted to the control unit 4a of the control device 4. The control device 4 then analyzes (performs analysis of) the data from the first optical information acquiring unit 120. In the present embodiment, whether or not the second optical information acquiring unit 160, to be described later, carries out the analysis is determined based on the analysis result.

The lamp unit 130 supplies light having five types of wavelengths used in the optical measurement performed by the first optical information acquiring unit 120 and the second optical information acquiring unit 160.

The reagent dispensing arm 140 is arranged to mix the reagent to the sample in the cuvette 200 by dispensing the reagent in a reagent container (not shown) mounted on the rotation transport unit 100 to the cuvette 200 held in the rotation transport unit 100. The reagent is added to the sample in which the optical measurement by the first optical information acquiring unit 120 is terminated to prepare the measurement specimen.

The cuvette moving unit 150 moves the cuvette 200 between the rotation transport unit 100 and the second optical information acquiring unit 160.

The second optical information acquiring unit 160 warms the measurement specimen prepared by adding the reagent to the sample, and measures the optical information from the measurement specimen. The second optical information acquiring unit 160 carries out the optical measurement (actual measurement) under a plurality of conditions with respect to the measurement specimen in the cuvette 200. The second optical information acquiring unit 160 is electrically connected to the control unit 4a of the control device 4, where the acquired data (optical information) is transmitted to the control unit 4a of the control device 4. Thus, in the control device 4, the data (optical information) transmitted from the second optical information acquiring unit 160 is analyzed based on the analysis result of the data (optical information) from the first optical information acquiring unit 120, which is acquired in advance, and displayed on the display unit 4b.

[4.2 Cuvette Supply Mechanism Section 6]

Figure 3:
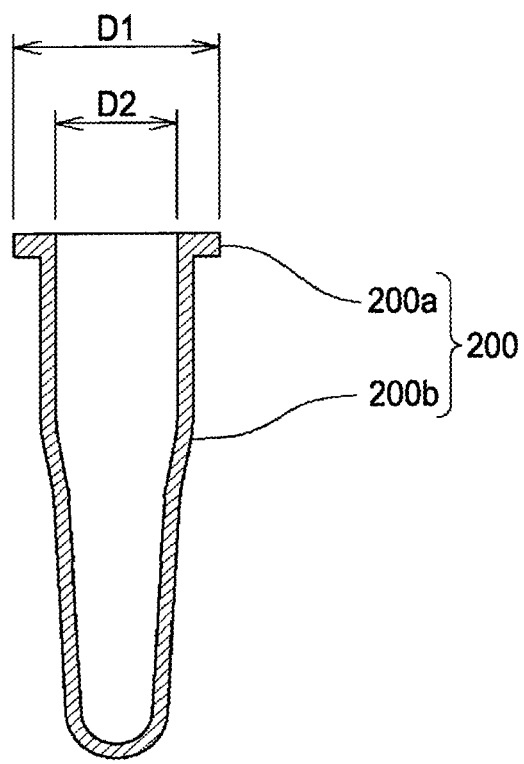
FIG. 3 is a cross-sectional view of a cuvette.

The cuvette supply mechanism section 6 is arranged to supply a plurality of cuvettes 200 (see FIG. 3) inserted in an offhand manner by the user one at a time to the rotation transport unit 100 of the analysis mechanism section 7. As shown in FIG. 3, the cuvette 200 is configured by a flange portion 200a having a diameter D1 (about 10 mm) and a body portion 200b having a diameter D2 (about 8 mm) smaller than the diameter D1. The cuvette 200 has a length of about 30 mm.

As shown in FIG. 4 to FIG. 7, the cuvette supply mechanism section 6 includes an cuvette storage 9 for accumulating the cuvette 200 inserted from the insertion port 5b (see FIG. 1), a carry-out unit 20 for receiving the cuvette 200 accumulated in the cuvette storage 9 and carrying out the same to outside the cuvette storage 9, a transfer unit 300 for transferring the cuvette 200 existing at the bottom of the cuvette storage 9 towards the carry-out unit 20, and an arrangement unit 90 for arranging the cuvette 200 carried out by the carry-out unit 20 at a predetermined position (rotation transfer unit 60 to be described later).

The cuvette storage 9 deposits and accumulates one part (container mounting portion 304 to be described later) of the transfer unit 300 configuring the bottom surface of the cuvette storage 9. The transfer unit 300 transfers the cuvette 200 existing at the bottom of the cuvette storage 9 towards a receiving region A1 where the carry-out unit 20 receives the cuvette 200. In the present embodiment, a transfer direction (direction of arrow X) in which the transfer unit 300 transfers the cuvette 200 towards the receiving region A1 is the front side in the front and back direction, the opposite direction is the back side in the transfer direction, and the orthogonal direction of the transfer direction is the left and right direction.

Describing the outline of the arrangement unit 90 first, the arrangement unit 90 includes a receiving portion 30 for receiving the cuvette 200 carried out by the carry-out unit 20, a cuvette sending portion 40 for sending out the cuvette 200 one at a time from the receiving portion 30, and a transport arrangement portion 50 for transporting the cuvette 200 sent out from the sending portion 40 to the rotation transfer unit 60, to be described later.

As shown in FIG. 2, the measurement mechanism section 2 includes the rotation transfer unit 60 arranged at the lower end of the transport arrangement portion 50, and a supply catcher unit (container transport unit) 70 arranged with a predetermined spacing from the rotation transfer unit 60, in addition to the cuvette supply mechanism section 6 and the analysis mechanism section 7.

[4.2.1 Cuvette Storage 9]

Figure 4:
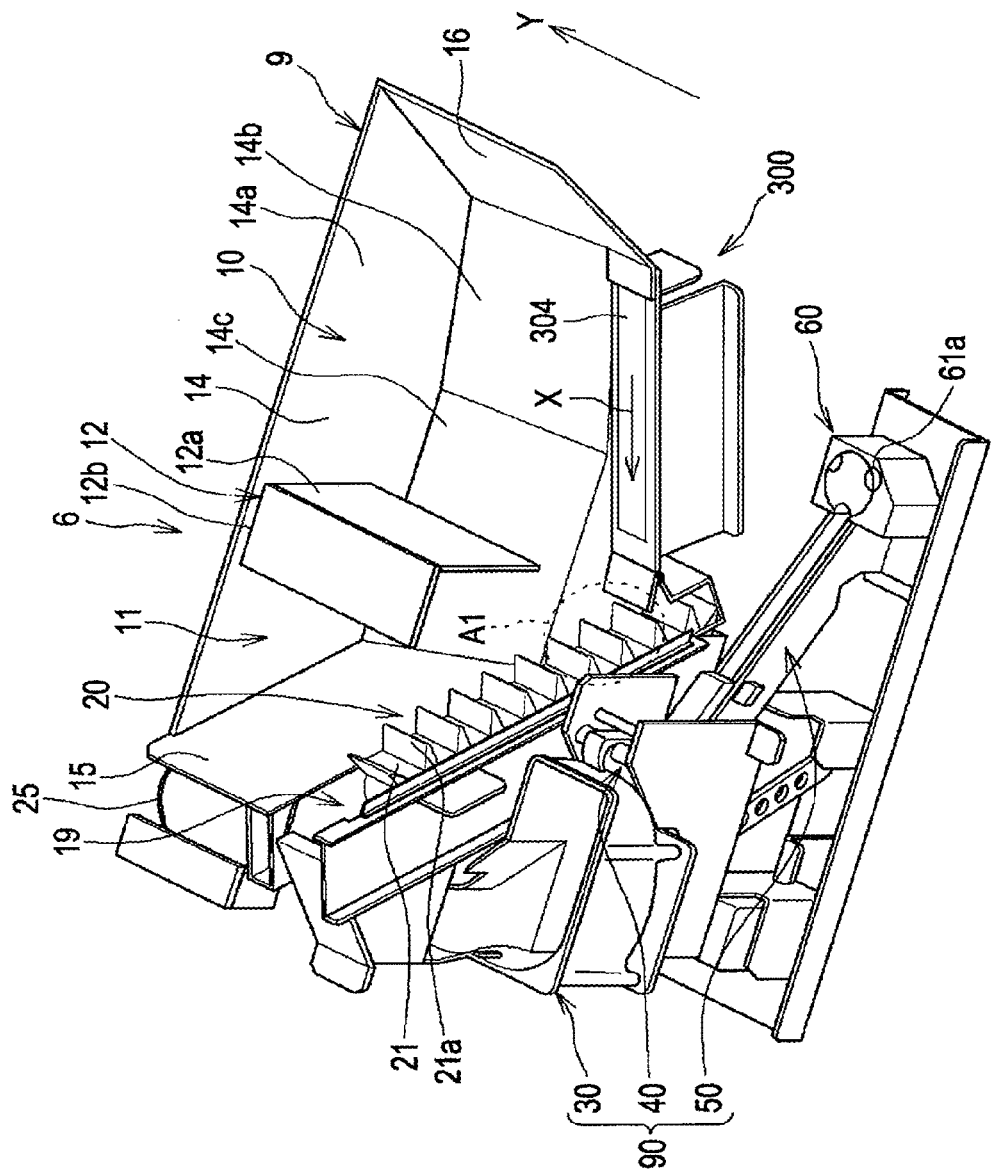
FIG. 4 is a perspective view of a cuvette supply mechanism section (container supplying device)

As shown in FIG. 4 to FIG. 7, the cuvette supply mechanism section 6 includes the cuvette storage 9 for accumulating the cuvette 200. The cuvette storage 9 is configured as a container in which the upper side is opened, and includes a first side surface 13 and a second side surface 14 facing each other in the left and right direction, and a third side surface 15 and a fourth side surface 16 facing each other in the front and back direction. In FIG. 4, a state in which the first side surface 13 on one side is removed is shown to describe the state inside the cuvette storage 9.

Figure 5:
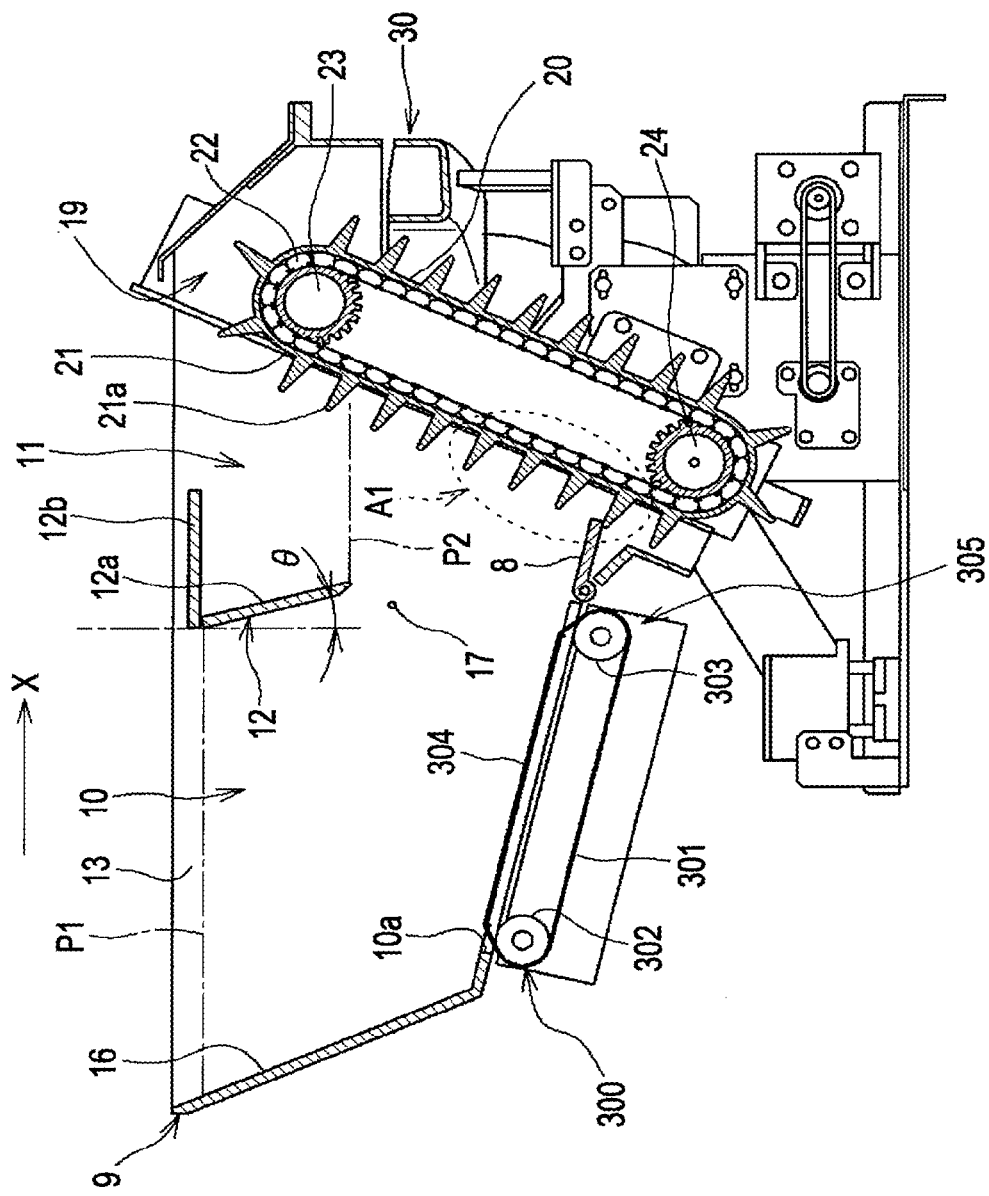
FIG. 5 is a cross-sectional view of the cuvette supply mechanism section seen from the side.
Figure 6:
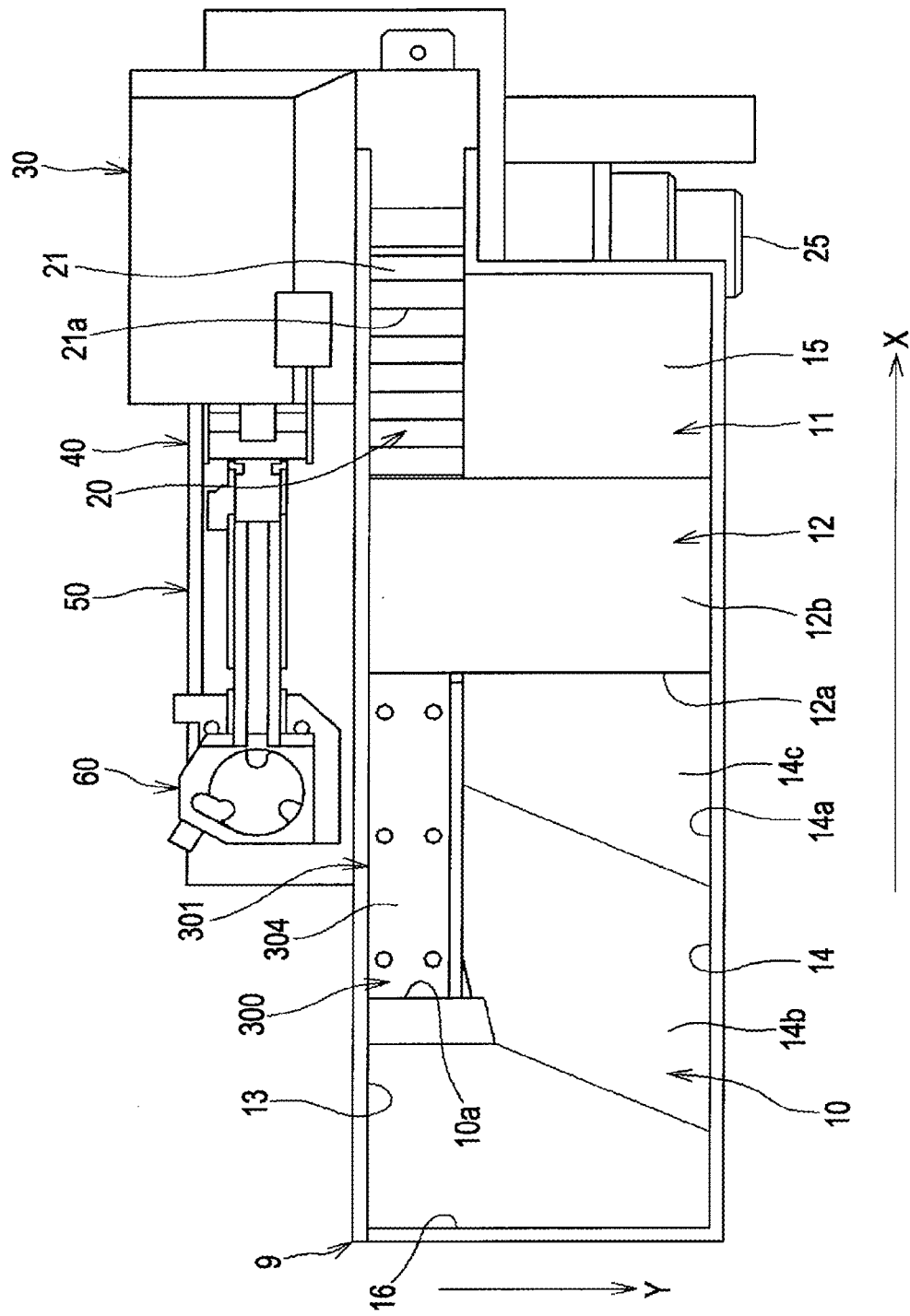
FIG. 6 is a plan view of the cuvette supply mechanism section.
Figure 7:
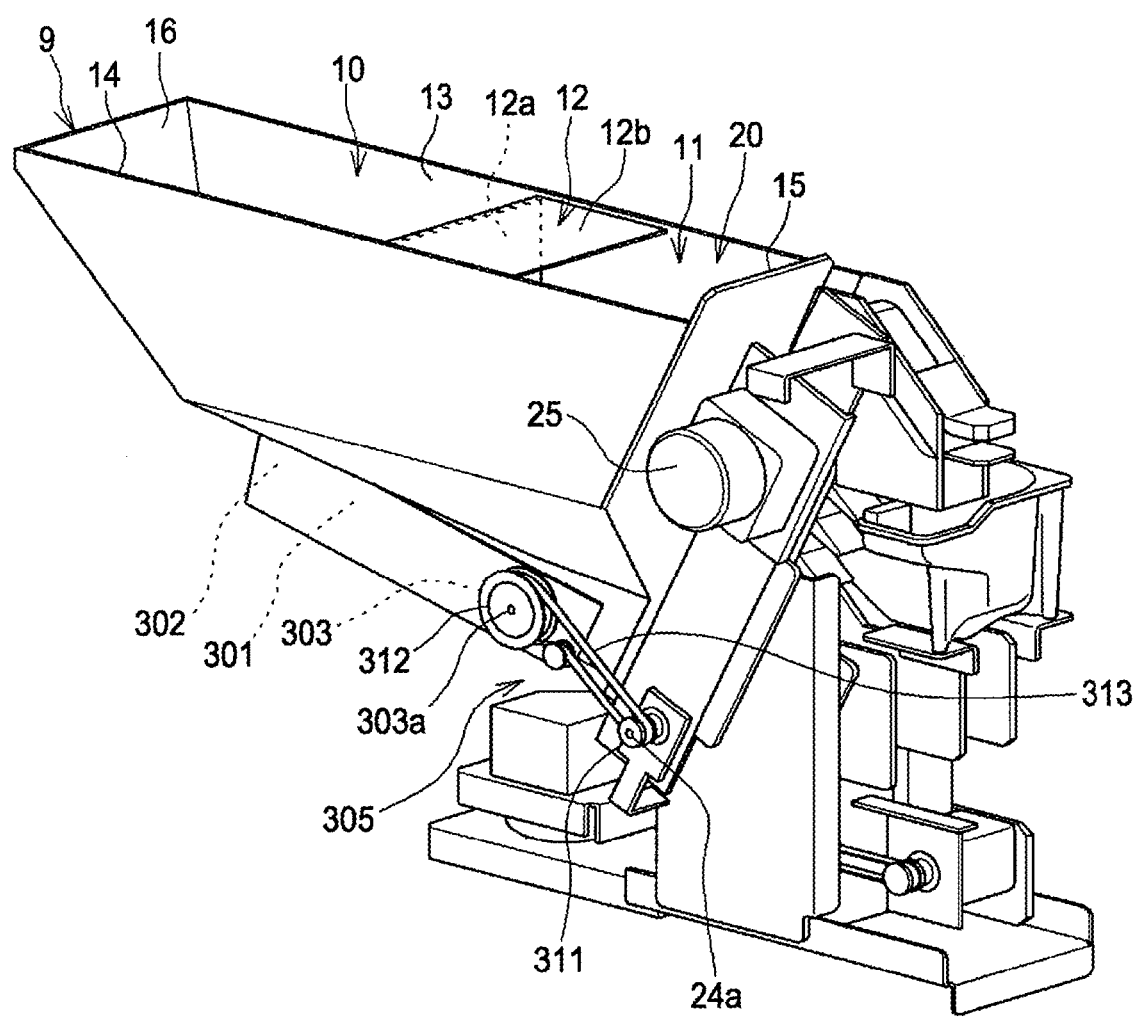
FIG. 7 is another perspective view of the cuvette supply mechanism section.

A first space 10 is formed in the cuvette storage 9. That is, the cuvette storage 9 is defined to the first space 10 and a second space 11 by a partitioning member 12. The partitioning member 12 partitions such that the capacity of the first space 10 becomes larger than that of the second space 11. As shown in FIG. 5, the partitioning by the partitioning member 12 is a range from the intermediate part to the upper part in the up and down direction of the cuvette storage 9, where the first space 10 and the second space 11 are connected at the lower part.

As shown in FIG. 2, the cuvette storage 9 and the first space 10 have an elongate shape that is long in the transfer direction (direction of arrow X) of the cuvette 200 and short in the orthogonal direction (direction of arrow Y) of the transfer direction in plan view at the upper part, the intermediate part and the lower part (bottom).

The first space 10 has an opening on the upper side of the space surrounded by the partitioning member 12, the fourth side surface 16, the first side surface 13, and the second side surface 14, which opening is the insertion port 5b (see FIG. 1) in the present embodiment. The cuvette 200 inserted from the insertion port 5b is passed through the insertion port 5b and accumulated in the cuvette storage 9. The second space 11 is connected to the insertion port 5b through only the first space 10. Therefore, the cuvette 200 inserted from the insertion port 5b is not directly inserted to the second space 11.

The cuvette storage 9 lowers the inserted cuvette 200 by its own weight, and accumulates the lowered cuvette 200 in great numbers. For instance, even if 2000 cuvettes 200 are inserted at one time, such cuvettes 200 can be collectively accumulated.

The partitioning member 12 has a function serving as a regulation member of regulating the cuvette 200 at the upper layer part of a great number of cuvette groups accumulated in the first space 10 of the cuvette storage 9 from rolling down towards the receiving region A1. The transfer unit 300 transfers the cuvette 200 existing at the bottom of the first space 10 of the cuvette storage 9 towards the receiving region A1. A specific configuration of the transfer unit 300 will be described later.

The first side surface 13 is a perpendicular surface formed to a planar shape as a whole. The second side surface 14 includes an upper side surface portion 14a parallel to the first side surface 13, and intermediate side surface portions 14b, 14c extending inclined from the lower end of the upper side surface portion 14a towards the bottom.

The third side surface 15 is positioned on the front surface side of the cuvette storage 9, and the fourth side surface 16 is positioned on the back surface side. The third and fourth side surfaces 15, 16 are respectively inclined such that the opposing spacing becomes smaller towards the lower side.

Therefore, in the cuvette storage 9, the first side surface 13, which is one side of the first side surface 13 and the second side surface 14 facing each other, has an inclined surface (intermediate side surface portion 14b, 14c) that narrows the cuvette storage 9 towards the bottom.

Thus, even if the upper part side of the cuvette storage 9 is enlarged in the left and right direction, the inserted cuvettes 200 can be easily collected towards the bottom by the inclined surface, and as a result, the cuvettes 200 can be reliably transferred by the transfer unit 300 positioned on the bottom surface side. In other words, the upper part side of the cuvette storage 9 can be made as wide as possible while ensuring the transfer ability of the cuvette 200 by the transfer unit 300, and the accumulation amount of the cuvette 200 can be increased.

The partitioning member 12 has an L shape with a substantially vertical plate shaped first member 12a and a horizontal second member 12b, and is arranged in the cuvette storage 9 opened to the upper side. Both left and right sides of the partitioning member 12 are joined with the first and second side surfaces 13, 14.

As shown in FIG. 5, the first member 12a is slightly inclined (inclination angle θ) with respect to the vertical surface, and is inclined towards the receiving region A1 side with advancement to the lower side. The first member 12a is substantially parallel to the fourth side surface 16, and the dimension in the front and back direction of the cuvette storage 9 is suppressed from becoming narrower towards the lower side. On the other hand, the second space 11 formed between the first member 12a and the third side surface 15 (and annular belt 301, to be described later, horizontally in line with the third side surface 15) has a shape that becomes wider towards the upper side.

[4.2.2 Carry-Out Unit 20]

In FIG. 5, the carry-out unit 20 includes an annular belt 21 including a plurality of holding plates 21a, a chain 22 to which the annular belt 21 is attached, upper and lower sprockets 23, 24 engaged with the chain 22, and a motor 25 (see FIG. 7) for rotationally driving the sprocket 23. When the motor 25 rotates the sprocket 23, the annular belt 21 that received the rotation power from the sprocket 23 rotates. The annular belt 21 includes a belt with projection (holding plate). The drive portion of the carry-out unit 20 is configured by the chain 22, the sprockets 23, 24 and the motor 25.

The cuvette 200 is lifted up and held when the cuvette 200 is placed on the holding plate 21a. That is, the holding plate 21 becomes a container holder for holding the cuvette 200 when carrying out the cuvette 200.

The annular belt 21 is arranged lined in the left and right direction with the third side surface 15 (see FIG. 6), and the annular belt 21 is arranged from the bottom to the upper part of the second space 11.

The holding plate 21a normally has a size in which one to three cuvettes 200 can be stably mounted. The direction of the cuvette 200 held on the holding plate 21a does not need to be constant.

When the annular belt 21 is rotated, the cuvette 200 near the bottom of the second space 11 can be received by the holding plate 21, and thus the region near the bottom is the receiving region A1.

The cuvette 200 held by the holding plate 21a and carried out to the upper side is dropped to the side opposite to the second space 11 with the rotation of the annular belt 21. A receiving portion 30 is arranged at the destination to which the cuvette 200 is dropped, which receiving portion 30 receives the cuvette 200 carried out through the second space 11 from the first space 10.

Therefore, the carry-out unit 20 can lift up the cuvette 200 near the bottom of the first space 11 to the carry-out port 19 on the upper side and carry out the same to the receiving portion 30 side.

[4.2.3 Transfer Unit 300]

As shown in FIG. 5, the transfer unit 300 includes a container mounting portion 304 exposed at the bottom of the first space 10 and mounted with the cuvette 200 existing at the bottom, and a drive portion 305 for moving the container mounting portion 304 to the receiving region A1 side and transferring the cuvette 200 mounted on the container mounting portion 304 to the receiving region A1 side to provide a moving force towards the receiving region A1 side with respect to the cuvette 200 existing at the bottom of the first space 10 of the cuvette storage 9.

Specifically describing, the transfer unit 300 includes an annular belt 301 bridged between pulleys 302, 303 arranged on the back side and the front side in the front and back direction, and the cuvette storage 9 of the present embodiment includes an opening 10a where the bottom surface is entirely opened, where the annular belt 301 is exposed to the cuvette storage 9 from the opening 10a. Therefore, the container mounting portion 304 becomes the portion towards the receiving region A1, that is, the upper side portion of the annular belt 301 of the annular belt 301, and such upper side portion of the annular belt 301 becomes the bottom surface in the first space 10 of the cuvette storage 9. The annular belt 301 includes a flat belt.

The opening 10a is formed to an elongate shape from the lower end of the fourth side surface 16 to the annular belt 21 of the carry-out unit 20. The bottom surface of the cuvette storage 9 is configured by the upper side portion of the annular belt 301 arranged at the opening 10a and a transfer member 8, to be described later.

Therefore, the container mounting portion 304 configures the bottom surface in the first space 10 of the cuvette storage 9, so that the inserted cuvettes 200 are not concentrated at one area at the lower side of the partitioning member 12 and the receiving region A1 but are spread and mounted on the container mounting portion 304.

As shown in FIG. 5, the upper side portion of the annular belt 301 is configured as the inclined surface that becomes lower towards the receiving region A1 side.

The drive portion 305 includes a motor for rotating the annular belt 301. In the present embodiment, the motor of the drive portion 305 arranged in the transfer unit 300 is the motor 25 (see FIG. 7) arranged in the carry-out unit 20, and thus the motor is commonly used by the transfer unit 300 and the carry-out unit 20.

The common use of the motor will be specifically described. The rotation shaft 24a (see FIG. 7) of the sprocket 24 (see FIG. 5) of the carry-out unit 20 is extended axially outward, and the pulley 303 receives the rotation power from the rotation shaft 24a. That is, in FIG. 7, a first transmission pulley 311 is attached in an integrally rotatable manner to the rotation shaft 24a, a second transmission pulley 312 is attached in an integrally rotatable manner to the rotation shaft 303a of the pulley 303 for the annular belt 301, and a transmission belt 313 is bridged between the first transmission pulley 311 and the second transmission pulley 312. The second transmission pulley 312 has a greater diameter than the first transmission pulley 311, and can decelerate the rotation of the rotation shaft 24a to transmit it to the pulley 303. Therefore, the annular belt 21 of the carry-out unit 20 rotates at higher speed than the annular belt 301 of the transfer unit 300, and the movement speed of the cuvette 200 by the carry-out unit 20 can be made greater than the movement speed of the cuvette 200 by the transfer unit 300.

Therefore, when the sprocket 23 for the carry-out unit 20 is rotated by the rotation of the motor 25, the annular belt 301 of the transfer unit 300 can be rotated through the annular belt 21, the chain 22, the sprocket 24, the rotation shaft 24a, and the like. The cuvette 200 existing at the bottom in the first space 10 of the cuvette storage 9 is transferred to the receiving region A1 side by the rotation of the annular belt 301. The drive portion 305 of the transfer unit 300 is configured to include the pulleys 302, 303, the second transmission pulley 312, the first transmission pulley 311, and the transmission belt 313.

As described above, the carry-out unit 20 includes the motor 25 as a power source for driving the holding plate 21a of the annular belt 21, where the drive portion 305 of the transfer unit 300 is driven by the power of the motor 25. Therefore, the carry-out unit 20 and the transfer unit 300 are driven by the common motor 25, so that the carry-out unit 20 and the transfer unit 300 can synchronously carry out the operation and stop thereof.

In the present embodiment, the transfer member 8 (FIG. 5) for transferring the cuvette 200 is arranged on the front side of the container mounting portion 304. The transfer member 8 includes a plate member, where the cuvette 200 transferred on the annular belt 301 is sent to the transfer member 8, and can be placed on the holding plate 21a of the carry-out unit 20 through the transfer member 8. The transfer member 8 can be turned up and down with the back side as the center, and has a length in the front and back direction capable of being placed on the distal end of the holding plate 21a. The transfer member 8 is pushed up and turned upward with the rise of the holding plate 21a, but the transfer member 8 is turned downward and dropped and is placed on the distal end of the holding plate 21a underneath when the holding plate 21a is separated from the distal end of the holding plate 21a. In the present embodiment, the bottom surface of the second space 11 is configured by the transfer member 8.

According to the cuvette storage 9, the carry-out unit 20, and the transfer unit 300 having the above configuration, some of the great number of cuvettes 200 inserted and accumulated in the cuvette storage 9 are passed through the opening formed at the lower side of the partitioning member 12 by the transfer unit 300, transferred from the first space 10 to the second space 11, and accumulated in the second space 11. Even if the first space 10 is filled with a great number of cuvettes 200 up to near the upper end, the cuvettes 200 can be suppressed from rolling down by its own weight to the second space 11 by the partitioning member 12.

Thus, the second space 11 is not filled up to near the upper part even if a great amount of cuvettes 200 is accumulated in the first space 10. Therefore, even if the cuvette 200 is in great amount in the first space 10, the cuvette 200 exists only near the bottom in the second space 11 and the cuvettes 200 are not accumulated in the upper space.

The carry-out port 19 through which the cuvette 200 passes when the cuvette 200 is carried out to the receiving portion 30 side is arranged at the upper part of the second space 11, and the cuvette 200 accumulated near the bottom of the second space 11 is lifted upward in the second space 11 by the carry-out unit 20 and carried out from the carry-out port 19 towards the receiving portion 30.

[4.2.4 Arrangement Unit 90]

Figure 8:
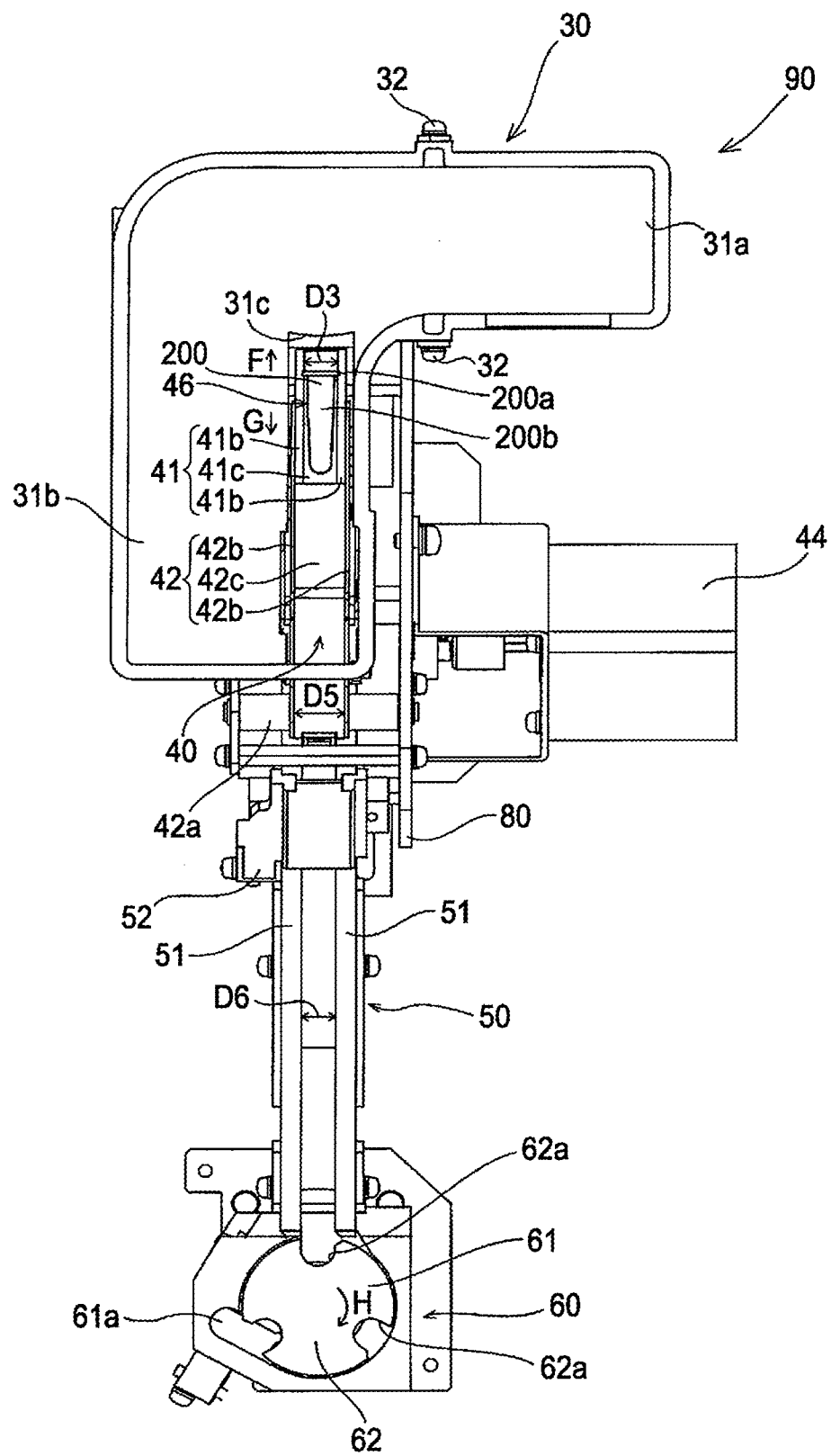
FIG. 8 is a plan view showing a configuration of an arrangement unit.
Figure 9:
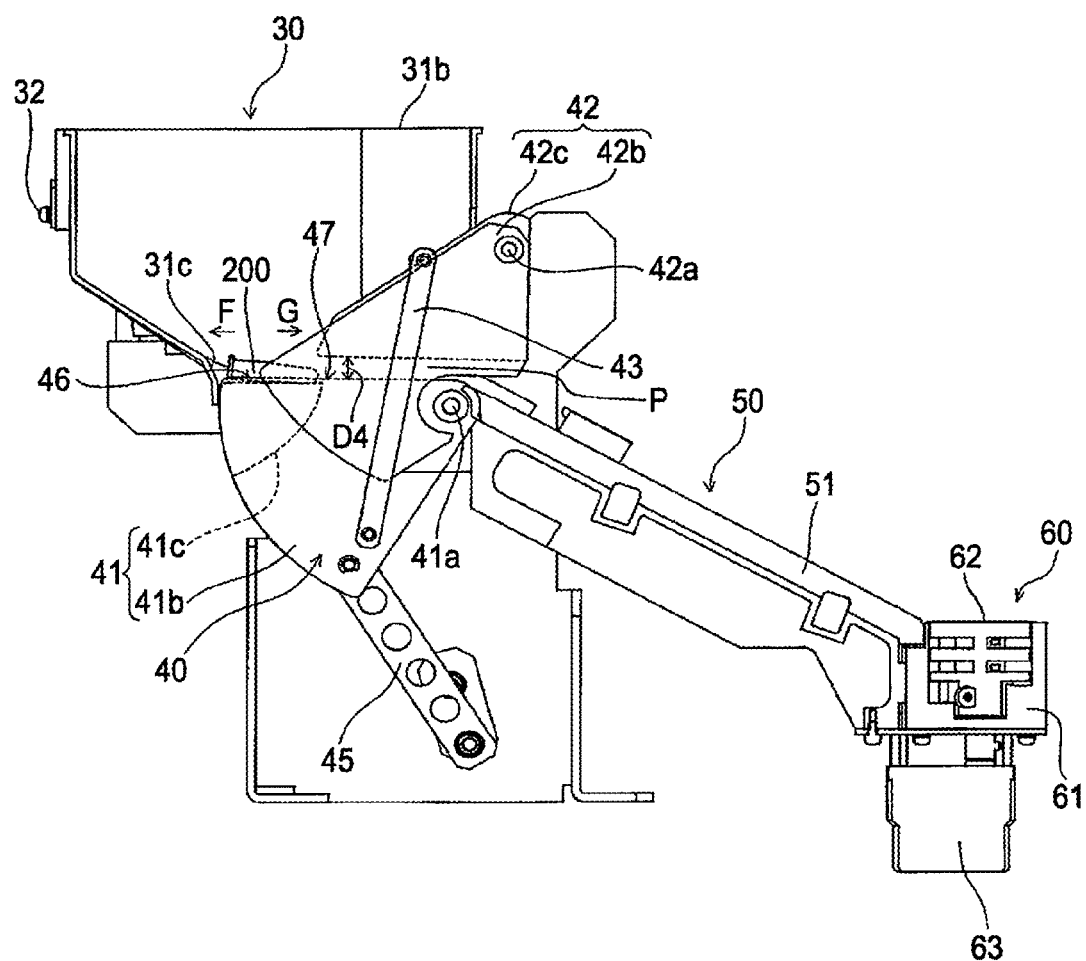
FIG. 9 is a side view showing a configuration of the arrangement unit.
Figure 10:
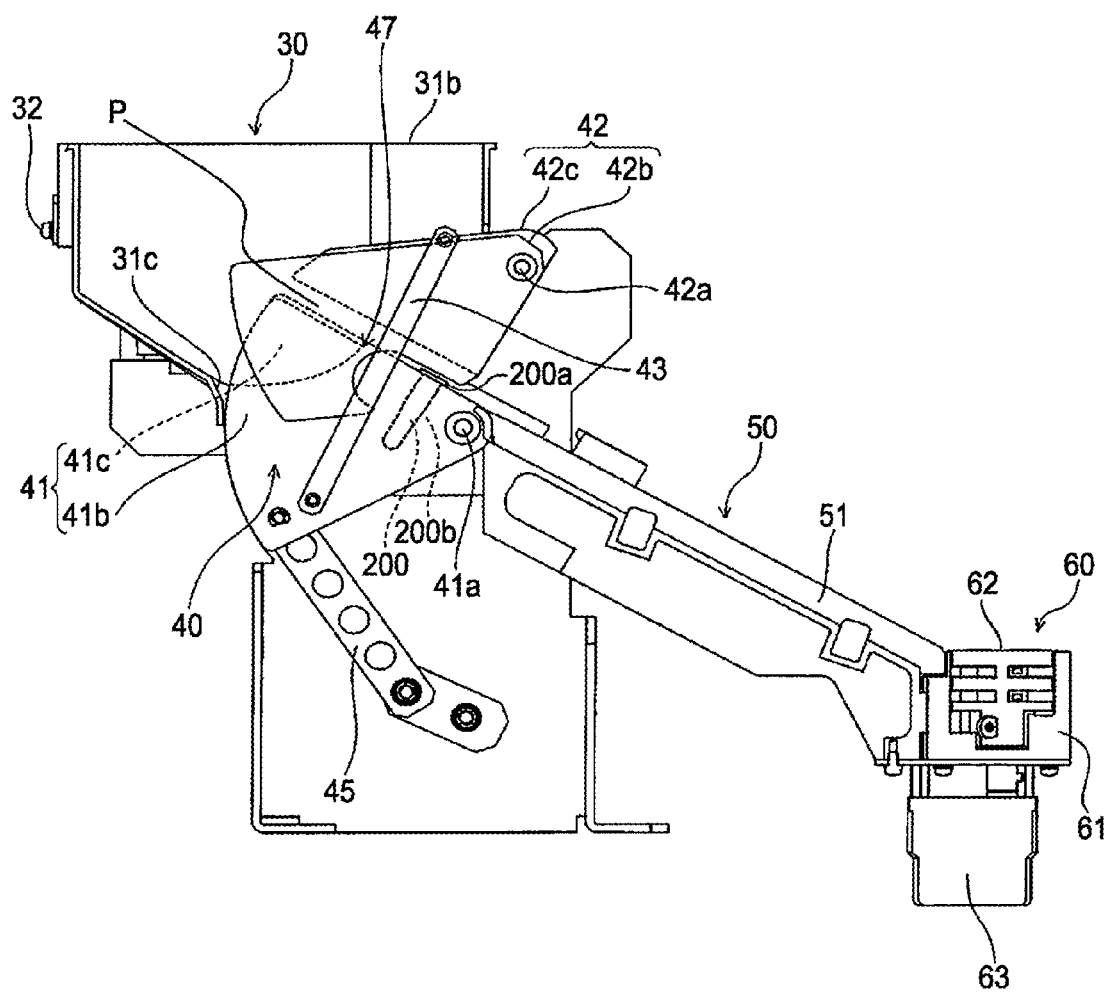
FIG. 10 is a side view showing a configuration of the arrangement unit.

In FIG. 8, FIG. 9, and FIG. 10, the arrangement unit 90 includes a receiving portion 30 for receiving the cuvette 200 carried out by the carry-out unit 20, a cuvette sending portion 40 of sending out the cuvette 200 one at a time from the receiving portion 30, and a transport arrangement portion 50 for transporting the cuvette 200 sent out from the sending portion 40 to the rotation transfer unit 60.

The receiving portion 30 includes a cuvette receiving part 31a and a cuvette accumulating part 31b, and has an L shape in plan view. The inner bottom surface of the receiving portion 30 is inclined downward from the cuvette receiving part 31a towards the cuvette accumulating part 31b, so that the cuvette 200 dropped from the annular belt 21 to the cuvette receiving part 31a is automatically moved to the cuvette accumulating part 31b.

The receiving portion 30 has a storage amount (about 100) of the cuvette 200 less than the storage amount (about 2000) of the cuvette 200 of the cuvette storage 9. A sensor 32 detects when the cuvette 200 stored in the receiving portion 30 becomes greater than or equal to a predetermined amount. In the present embodiment, when the sensor 32 makes the detection, the control unit 4a determines that the receiving portion 30 is full and stops the operation of the motor 25 (see FIG. 7) to stop the operation of the transfer unit 300 and the carry-out unit 20.

The cuvette sending portion 40 includes an oscillation rail 41 that can be turned with the turning shaft 41a as a center, an oscillation guide 42 that can be turned with another turning shaft 42a as a center, a link 43 for coupling and cooperatively moving the oscillation rail 41 and the oscillation guide 42, a motor 44, and an arm 45 for transmitting the drive force of the motor 44 to the oscillation rail 41. The arm 45 is rotated by the rotating motor 44, and the oscillation rail 41 and the oscillation guide 42 are reciprocatively oscillated.

The oscillation rail 41 has a pair of fan-shaped plates 41b made of metal and a spacer 41c made of resin fixed by being sandwiched by the pair of fan-shaped plates 41b. As shown in FIG. 8, a spacing (thickness of spacer 41c) D3 of the pair of fan-shaped plates 41b is smaller than the diameter D1 (see FIG. 3) of the flange portion 200a of the cuvette 20 and greater than the diameter D2 (see FIG. 3) of the body portion 200b.

The oscillation guide 42 has a pair of guide plates 42b arranged to contact the outer sides of the pair of fan-shaped plates 41b of the oscillation rail 41, and a spacer 42c made of resin fixed by being sandwiched by the guide plates 42b. A path P through which the cuvette 200 can pass is formed between the oscillation rail 41 and the oscillation guide 42.

As shown in FIG. 9, the spacing D4 of the spacer 41c of the oscillation rail 41 and the spacer 42c of the oscillation guide 42 is greater than the diameter D1 (see FIG. 3) of the flange portion 200a of the cuvette 200 but does not allow two cuvettes 200 to be arranged. As shown in FIG. 8, the spacing D5 of the pair of guide plates 42b is greater than the diameter D1 (see FIG. 3) of the flange portion 200a of the cuvette 200 but does not allow two cuvettes 200 to be arranged. Therefore, only one cuvette 200 is arranged at the sending position 46 (see FIG. 8 and FIG. 9).

As shown in FIG. 8 and FIG. 9, the direction of the cuvette 200 is parallel to the oscillation rail 41 at the sending position 46. The open end of the cuvette 200 may be directed in either direction, the direction of the arrow F or the direction of the arrow G. When the cuvette 200 is moved on the oscillation rail 41, the spacer 41c of the oscillation rail 41 is cut at the position 47 in the middle of the fan-shaped plate 41b, as shown in FIG. 10, and hence the cuvette 200 has the closed end lower downward by its own weight at the position 47. As described above, the interval D3 (see FIG. 8) is smaller than the diameter D1 (see FIG. 3) of the flange portion 200a of the cuvette 200 and greater than the diameter D2 (see FIG. 3) of the body portion 200b, and thus the flange portion 200a is supported by the pair of fan-shaped plates 41b, as shown in FIG. 10. Thus, the cuvette sending portion 40 causes the open end of the cuvette 200 to face upward in the process of passing the cuvette 200 through the path P.

Therefore, when the oscillation rail 41 and the oscillation guide 42 are oscillated with the cuvette 200 arranged at the sending position 46, the cuvette 200 is passed through the path P and transported to the transportation rail 51 of the transport arrangement portion 50, as shown in FIG. 9 and FIG. 10.

The transport arrangement portion 50 includes a pair of transportation rails 51 configuring the path for transporting the cuvette 200 to the rotation transfer unit 60 or a predetermined position, and a reflective sensor 52. The pair of transportation rails 51 are arranged in parallel to each other with a spacing smaller than the diameter D1 of the flange portion 200a of the cuvette 200 (see FIG. 3) and greater than the diameter D2 of the body portion 200b of the cuvette 200. The cuvette 200 that passed through the path P moves while slidably dropping towards the rotation transfer unit 60 with the flange portion 200a engaged to the upper surfaces of the pair of transportation rails 51.

The transportation rail 51 can accommodate the cuvette 200 by a predetermined number lined in a line, where when the number of cuvettes 200 accommodated in the transportation rail 51 becomes greater than or equal to a predetermined number, this is detected by the sensor 52 (see FIG. 8). In the present embodiment, when the sensor 52 carries out the detection, the control unit 4a stops the operations of the sending portion 40, the transfer unit 300, and the carry-out unit 20. Thus, the transfer from the first space 10 to the second space 11 and the carry out from the second space 11 to the receiving portion 30, as well as the sending from the receiving portion 30 to the transfer arrangement portion 50 of the cuvette 200 are stopped.

On the contrary, when the sensor 52 no longer detects the cuvette 200, the control unit 4a operates the sending portion 40 and sends out one cuvette 200. Furthermore, if the sensor 52 does not detect the cuvette even if the sending portion 40 is operated for a constant time, the transfer unit 300 and the carry-out unit 20 are operated while operating the sending portion 40. This is when the cuvette 200 does not exist in the receiving portion 30, and the receiving portion 30 can be replenished with the cuvette 200 by operating the transfer unit 300 and the carry-out unit 20.

That is, the sensor (detection unit) 52 is a sensor for detecting presence/absence of the cuvette 200 to be arranged on the rotation transfer unit 60 or a predetermined position on the transportation rail 51, where the control unit 4a (control means) can alternatively switch between drive and non-drive for the sending portion 40, the transfer unit 300 and the carry-out unit 20 according to the detection result of the sensor 52.

A state in which a constant number of cuvettes 200 is waiting on the transportation rail 51 on a steady basis is thereby obtained.

[4.3 Rotation Transfer Unit 60 and Supply Catcher Unit 70]

The rotation transfer unit 60 rotatably transfers the cuvette 200 slidably dropped from the transportation rail 51 to a waiting position at where it can be gripped by the supply catcher unit 70. The rotation transfer unit 60 includes a supporting table 61, a rotatable rotary table 62 attached to the supporting table 61, and a motor 63 for driving the rotary table 62. When the rotary table 62 is rotated by the motor 63, the cuvette 200 fitted to three cutouts 62a of the rotary table 62 is transported to a cutout 61a (waiting position) of the supporting table 61.

In FIG. 2, the supply catcher unit (container transport unit) 70 transports the cuvette 200 transported to the waiting position (cutout 61a) by the rotation transfer unit 60 to the dispensing table 103 of the rotation transport unit 100 of the analysis mechanism section 7, which is another area.

In the analysis mechanism section (optical detector) 7, the reagent dispensing arm 140 dispenses (supplies) the reagent in the reagent container (not shown) mounted on the rotation transport unit 100 to the cuvette 200 transported to the dispensing table 103 by the supply catcher unit 70 to mix the sample in the cuvette 200 and the reagent, whereby the optical detection of the sample (specimen) is carried out.

[4.4 Regarding Accumulation and Carry-Out of Cuvette in Cuvette Storage]

In FIG. 5, the first space 10 can be filled with the cuvette 200 up to the maximum accumulation position (upper end of cuvette group when about 2000 cuvettes are inserted) shown with P1. Thus, even if a great number of (about 2000) cuvettes 200 are inserted at one time, some of the cuvettes 200 (about more than a dozen to a few dozen) transferred by the transfer unit 300 are merely positioned near the receiving region A1 in the second space 11, and the cuvettes 200 are not filled up to the upper end of the second space 11. In FIG. 5, the upper end of the cuvette group accumulated in the second space 11 is shown with P2.

The accumulation position upper end P2 of the cuvette 200 in the second space 11 is a position lower than the maximum accumulation position P1 of the first space 10. Thus, the carry-out unit 20 can lift up the few number of cuvettes 200 in the second space 11 with the holding plate 21a, and can prevent an excessive amount of cuvettes 200 from being carried out.

That is, since the carry-out unit 20 is arranged at a steep slope (60 to 80 degrees) from the bottom part to the upper part of the second space 11, even if the cuvette 200 being transported on the holding plate 21a is in excess, some of the cuvettes 200 may be expected to fall off from the holding plate 21a and drop onto the bottom of the second space 11 while being transported to the carry-out port 19.

In other words, the number of cuvettes 200 that can be stably held by the holding plate 21a is a couple for one holding plate 21a, and thus even if the cuvette 200 of a number in which the holding by the holding plate 21a becomes unstable is lifted up by the holding plate 21a at one time, such cuvettes 200 are held in an unstable state and thus have a high probability of being dropped from the holding plate 21a before reaching the carry-out port 19 of the cuvette 200.

When the cuvettes 200 are carried out to the receiving portion 30 in great amount at one time, the following phenomenon tends to easily occur and the cuvette 200 may not be smoothly arranged at a predetermined position (rotation transfer unit 60).

As described with FIG. 8 to FIG. 10, the cuvette 200 carried out by the carry-out unit 20 is accumulated in the receiving portion 30, passed through the path P by the sending portion 40, and arranged at a predetermined position (rotation transfer unit 60). The path P has a size that allows only one cuvette 200 to pass, but if a great number of cuvettes 200 are accumulated in the receiving portion 30 at one time, the plurality of cuvettes 200 are pushed against the path P by the weight of the entire cuvette and the cuvettes tend to easily block the entrance of the path P.

Thus, even if a great number of cuvettes 200 are accumulated in the cuvette storage 9, the great number of cuvettes 200 can be suppressed from being carried out at one time to the receiving portion 30 by arranging the partitioning member 12 as in the present embodiment and limiting the number of cuvettes 200 that can be accumulated in the second space 11. Therefore, the user can increase the number of cuvettes 200 that can be inserted to the cuvette storage 9 at one time.

When the cuvette 200 of the second space 11 is lifted up by the carry-out unit 20, the number of cuvettes 200 in the second space (receiving region A1) reduces. The transfer unit 300 then forcibly transfers the cuvette 200 at the bottom of the cuvette storage 9 towards the carry-out unit 20 to supplement the cuvette 200 in the second space 11.

In the present embodiment, the transfer amount of the cuvette 200 by the transfer unit 300, that is, the rotation speed of the annular belt 301 is made smaller than the transfer amount of the cuvette 200 by the carry-out unit 20, that is, the rotation speed of the annular belt 21.

Thus, the transfer amount of the cuvette 200 to the receiving region A1 by the transfer unit 300 can be prevented from becoming an excess. As a result, the cuvette 200 is prevented from being supplied in excess to the receiving region A1 and the cuvette 200 from being stuck at the cuvette storage 9.

In the present embodiment, the rotation speed of the belt of the transfer unit 300 is made smaller than that of the carry-out unit 20 to have the transfer amount by the transfer unit 300 smaller than the transfer amount by the carry-out unit 20, but it is not particularly limited as long as there is a difference in the transfer amount. For instance, the frictional force of the belt of the transfer unit 300 may be made smaller than the frictional force of the belt of the carry-out unit 20, or the width of the belt of the transfer unit 300 may be made smaller than the width of the belt of the carry-out unit 20 to create a difference in the transfer amount.

Figure 12:
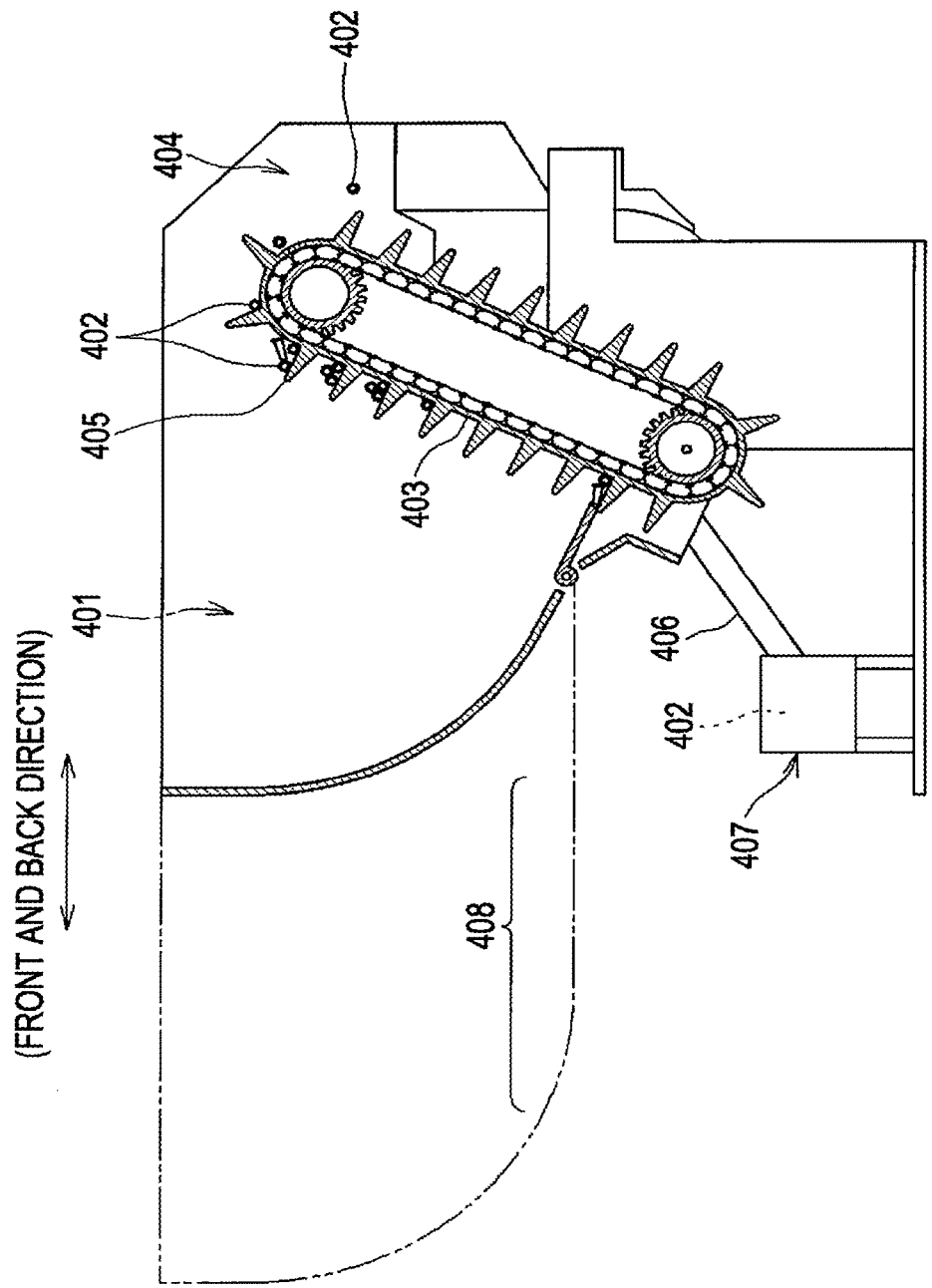
FIG. 12 is an explanatory view of a conventional cuvette supply mechanism section.

The cuvette supply mechanism section 6 according to the present embodiment configured as above has the following advantages compared to the conventional cuvette supply mechanism section. FIG. 12 is an explanatory view of the conventional cuvette supply mechanism section. In the conventional cuvette supply mechanism section, the capacity of the first cuvette storage 401 is increased to increase the number of cuvettes that can be accommodated in order to increase the number of cuvettes that can be inserted at one time by the user. In other words, in order to increase the capacity of the cuvette that can be inserted in the first cuvette storage 401 at one time by two times such as from 500 to 1000, the height of the first cuvette storage 401 can be doubled, but in this case, it is not convenient for the user since the position of the insertion port becomes high. Thus, consideration is made in enlarging the first cuvette storage 401 to two times in the front and back direction, as shown with a chain double dashed line in FIG. 12. In this case, however, when the number of cuvettes in the first cuvette storage 401 reduces, the cuvettes remain in the region 408 on the back side thereof, and all the cuvettes may not be smoothly supplied to the annular belt 403 side.

According to the cuvette supply mechanism section 6 of the present embodiment, on the other hand, the cuvette 200 existing at the bottom of the cuvette storage 9 can be transferred to the receiving region A1 side by the transfer unit 300 even if the cuvette storage 9 is enlarged in the front and back direction to increase the number of cuvettes 200 that can be inserted to the cuvette storage 9 at one time. In particular, even the cuvette 200 existing in the region on the back side of the cuvette storage 9 can be mounted on the annular belt 301 of the transfer unit 300 and transferred towards the receiving region A1. Therefore, according to the cuvette supply mechanism section of the present embodiment, the cuvettes can be smoothly supplied while increasing the number of cuvettes that can be inserted at one time.

The cuvette 200 at the upper layer part of a great number of cuvette groups accumulated in the cuvette storage 9 can be regulated from rolling down towards the receiving region A1 by the partitioning member 12. In other words, the transfer of the cuvette 200 towards the receiving region A1 side can be mainly performed by the transfer unit 300, and the cuvette 200 can be prevented from being unnecessarily collected on the receiving region A1 side.

Therefore, even if the number of cuvettes 200 that can be inserted to the cuvette storage 9 at one time is increased, the cuvette 200 accumulated in the cuvette storage 9 can be smoothly carried out towards the receiving portion 30 at an appropriate number by the carry-out unit 20, and the cuvette 200 that is carried out can be arranged in the rotation transfer unit 60 by the arrangement unit 90.

As a result, the cuvette 200 is arranged in the rotation transfer unit 60 and transported to the analysis mechanism section 7 by the supply catcher unit 70, so that the optical detection of the sample (specimen) can be sequentially carried out by the cuvette 200 according to the analysis mechanism section 7.

As shown in FIG. 5, in the present embodiment, a sensor 17 for detecting the accumulation height of the cuvette 200 is arranged in the cuvette storage 9 (first space 10 or second space 11). The sensor 17 is a light transmissive sensor having the position of a predetermined height from the bottom surface as a detection height, and transmits a detection signal to the control unit 4a when the number of cuvettes 200 is reduced and the sensor 17 no longer detects the cuvette 200. That is, the reduction of the number of cuvettes 200 is detected. When the detection signal is transmitted to the control unit 4a, the control unit 4a makes a display on the display unit 4b to urge refill of the cuvette 200 to notify the user.

The present invention is not limited to the above embodiment, and various modifications may be made.

For instance, only the second side surface 14 has an inclined surface in the cuvette storage 9 in the embodiment described above, but both the first side surface 13 and the second side surface 14 facing each other may have an inclined surface, or at least one of which may have an inclined surface that narrows the cuvette storage 9 towards the bottom.

A case in which the transfer unit 300 and the carry-out unit 20 synchronously operate has been described in the above embodiment, but each unit may be independently operated. In this case, the control unit 4a (control means) alternately switch between drive and non-drive of only one of the transfer unit 300 or the carry-out unit 20 according to the detection result of the sensor (detection unit) 52 for detecting the presence/absence of the cuvette 200 to be arranged in the rotation transfer unit 60 on the transportation rail 51 in the arrangement unit 90.

Figure 13:
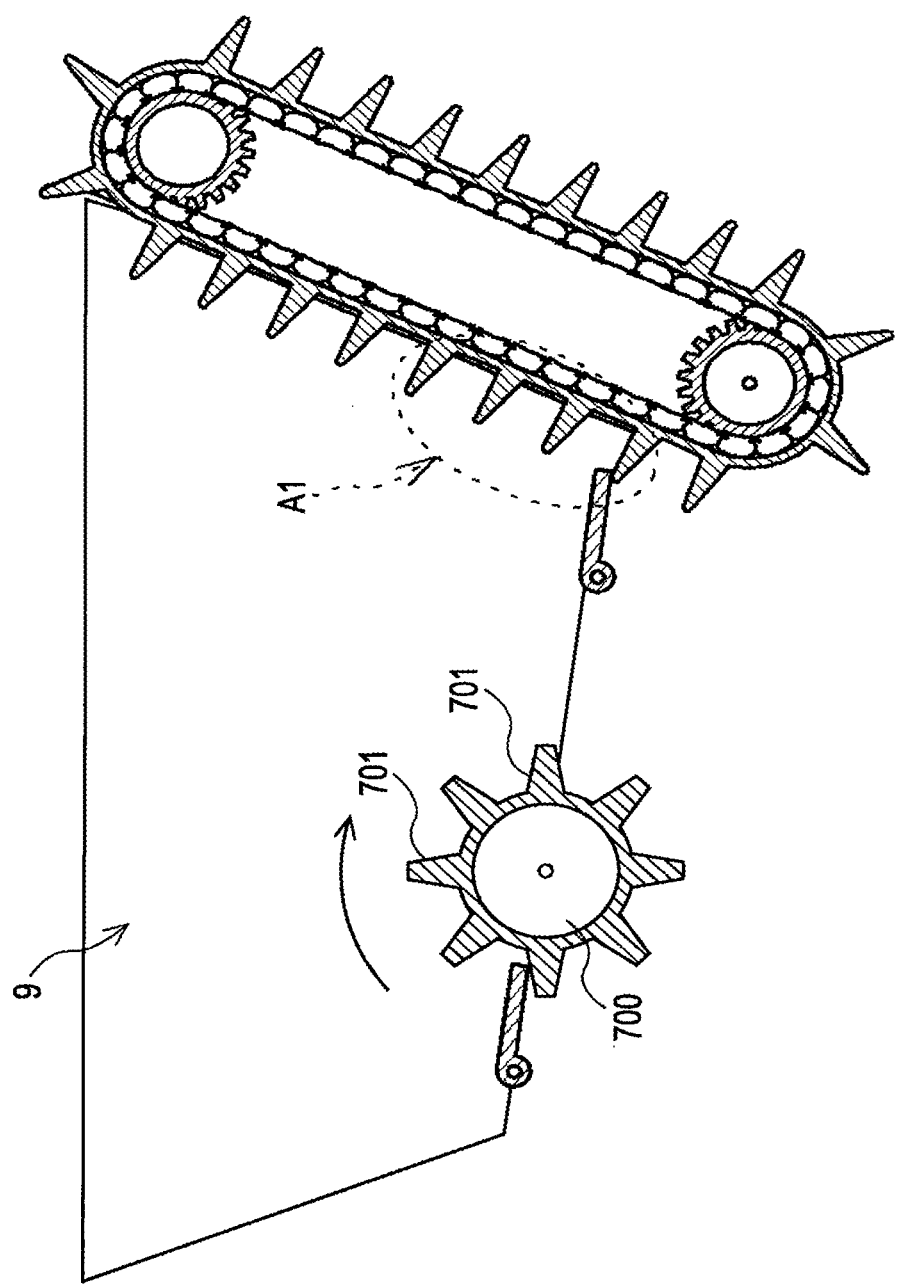
FIG. 13 is an explanatory view of another cuvette supply mechanism section (container supplying device).

Furthermore, a flat belt has been described as an example of the transfer unit in the embodiment described above, but the cuvette 200 accumulated in the cuvette storage 9 merely needs to be transferred towards the carry-out unit, and the mode of the transfer unit is not limited. For instance, as shown in FIG. 13, a gear 700 with a plurality of teeth 701 may be arranged at the bottom surface of the cuvette storage 9 and rotated in the direction indicated with an arrow in FIG. 13 to transfer the cuvette 200 to the receiving region A1 for the transfer unit.

Furthermore, the transfer unit 300 and the carry-out unit 20 are configured by separate transportation belts in the embodiment described above, but the present invention is not limited thereto, and the transfer unit 300 and the carry-out unit 20 may be configured with one belt.

A case in which the cuvette storage 9 has an opening 10a where the bottom surface is entirely opened, and the annular belt 301 is exposed to the interior of the cuvette storage 9 from such opening 10a has been described, but one part of the bottom surface of the cuvette storage 9 may be opened and the annular belt 301 may be exposed from such opening.

Figure 11:
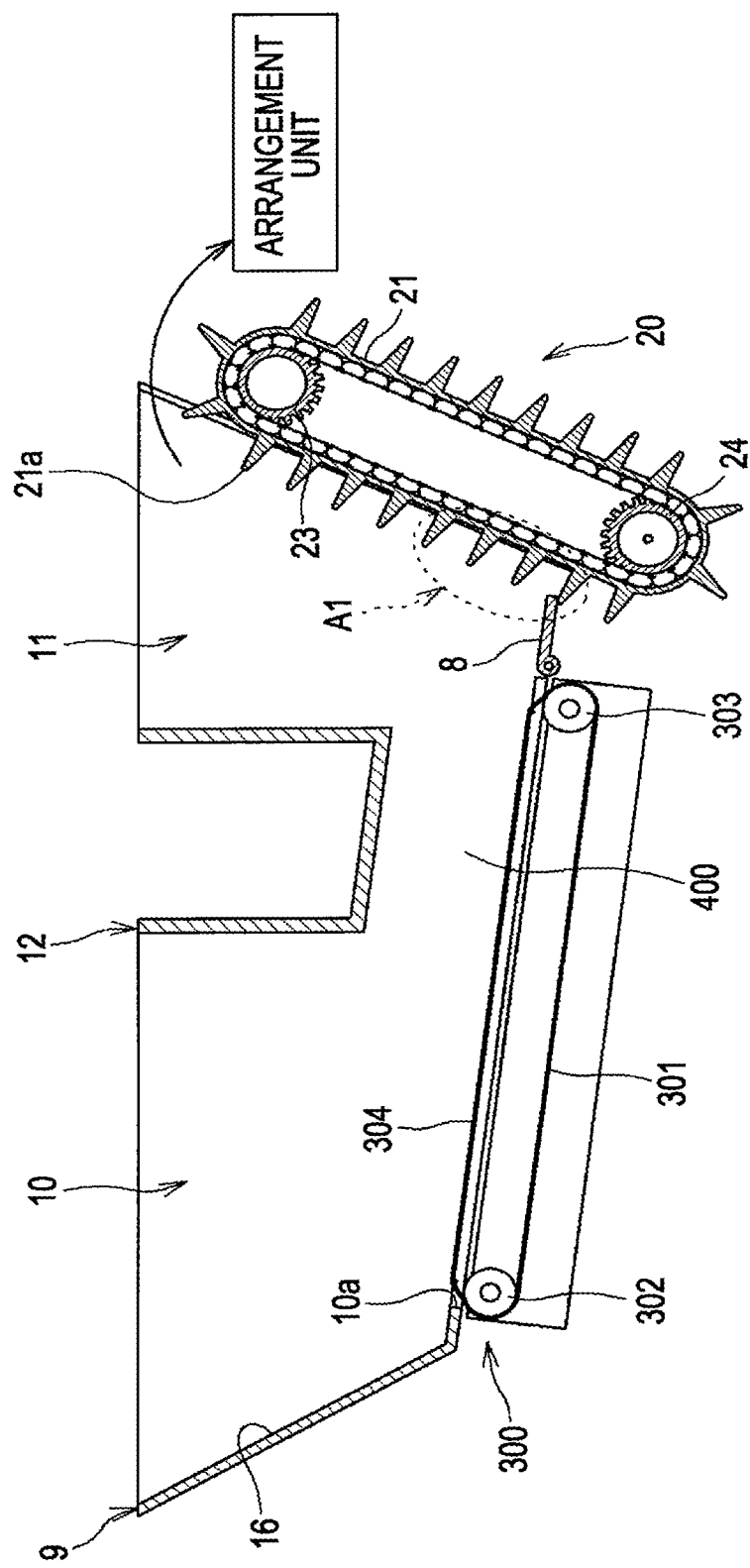
FIG. 11 is a cross-sectional view showing a variant of the cuvette supply mechanism section.

For instance, not limited to a mode in which the cuvette storage 9 is defined by the partitioning member 12 including a plate member, the inner wall of the cuvette storage 9 may be defined to the first space 10 and the second space 11 by the partitioning portion 12 depressed to the inner side, and such first space 10 and second space 11 may be coupled through a tunnel shaped passage 400, as shown in FIG. 11. In this case as well, the partitioning portion 12 functions as a regulation member for regulating the cuvette 200 at the upper layer part of a great number or cuvette groups accumulated in the first space 10 from rolling down to the receiving region A1 side.

In the embodiment described above, a configuration including the receiving portion 30, the cuvette sending portion 40, and the transport arrangement portion 50 has been described for the arrangement unit 90, but such configuration is not the sole case. The arrangement unit 90 may be in a mode in which the cuvette 200 is arranged at a predetermined position through only a series of passages (e.g., downhill slope path such as a dust shoot).

What is claimed is:

1. A specimen analyzer comprising: a cuvette supplying device, wherein the cuvette supplying device comprises:
    a cuvette storage for storing cuvettes,
    a carrier, provided inside the cuvette storage, for carrying the cuvettes in the cuvette storage outside the cuvette storage, the carrier includes an upper sprocket arranged at the bottom of the cuvette storage having a rotation shaft connected to first transmission pulley, a lower sprocket arranged on the upper side of the cuvette storage, a belt supported around the upper and lower sprockets, and a plurality of holding plates arranged at the periphery of the belt, and the container is carried from the upper sprocket towards the lower sprocket by the plurality of holding plates when the upper sprocket is driven;
    a transfer unit for conveying the cuvettes existing at the bottom of the cuvette storage towards the carrier, the transfer unit includes a mounting portion on which the cuvettes existing on the bottom of the cuvette storage are mounted and a drive section for rotationally driving the mounting portion to transfer the cuvettes on the mounting portion towards the carrier, the drive section includes a second transmission pulley operatively connected to the first transmission pulley and having a greater diameter than the first transmission pulley and can decelerate the rotation of the rotation shaft to transmit it to the second transmission pulley such that the carrier rotates at a higher speed than the transfer unit,
    an arranging section for arranging the cuvettes carried outside the cuvette storage by the carrier at a predetermined position;
    a partitioning member for regulating the cuvettes at an upper layer part of a stack of cuvettes in the cuvette storage from rolling towards the carrier;
    an optical detector for optically interrogating a specimen accommodated in the cuvette;
    a container transport unit for transporting the cuvette arranged at the predetermined position to the optical detector, a motor that is used in common to drive the drive section of the transfer unit and the upper sprocket of the carrier; and wherein the arranging section comprises:

a receiving portion configured to store the cuvettes carried by the carrier; and a transportation rail configured to accommodate the cuvettes stored in the receiving portion in a line, and to arrange the cuvette accommodated in the line at the predetermined position.

2. The specimen analyzer according to claim 1, wherein the cuvette storage is provided with an insertion port at the upper side through which a user drops cuvettes into the cuvette storage, and the cuvette storage randomly stores the cuvettes dropped through the insertion port.

3. The specimen analyzer according to claim 1, wherein the transfer unit includes:

the mounting portion being provided so as to be exposed at the bottom of the cuvette storage.

4. The specimen analyzer according to claim 3, wherein the transfer unit includes an annular belt between the second transmission pulley and another pulley arranged in a line directed towards the carrier.

5. The specimen analyzer according to claim 3, wherein the mounting portion is configured as an inclined surface that becomes lower towards the carrier.

6. The specimen analyzer according to claim 3, wherein a bottom surface of the cuvette storage is entirely or partially opened, and the mounting portion is exposed into the cuvette storage through the opening.

7. The specimen analyzer according to claim 1, wherein a transfer amount of the cuvettes by the conveyor is smaller than a transfer amount of the cuvettes by the carrier.

8. The specimen analyzer according to claim 3, wherein the cuvette storage is, in a plan view, an elongate shape that is long in the transfer direction of the cuvettes transferred by the transfer unit towards the carrier and short in the orthogonal direction of the transfer direction, and the mounting portion is arranged along the longitudinal direction of the cuvette storage.

9. The specimen analyzer according to claim 8, wherein the cuvette storage has an inclined surface in at least one of the side surfaces facing each other in the orthogonal direction so that the cuvette storage is narrowed.

10. The specimen analyzer according to claim 1, further comprising a detecting section for detecting presence or absence of the cuvette arranged at the predetermined position by the arranging section, and a controlling section for alternatively switching drive and non-drive of at least one of the transfer unit and the carrier according to a detection result of the detecting section.

11. The specimen analyzer according to claim 1, wherein the carrier is arranged in an inclined manner to move the cuvettes towards a diagonally upper side.

12. The specimen analyzer according to claim 1, wherein the arranging section includes a receiving portion for receiving the cuvettes dropped from the shoulders after passing the highest position.

13. The specimen analyzer according to claim 1, wherein the arranging section includes a sending portion for supplying the cuvette carried out by the carrier one at a time, and a transport arrangement portion for aligning the cuvettes supplied by the carrier.

14. The specimen analyzer according to claim 13, wherein the transport arrangement portion aligns the cuvettes such that an opening of the container is faced upward.

15. The specimen analyzer according to claim 1, wherein the partitioning member is inclined toward a receiving portion side with advancement to a lower side.

16. The specimen analyzer according to claim 1, wherein the transportation rail is configured to cause the open end of the cuvette to face upward.

17. The specimen analyzer according to claim 1, wherein the container transport unit comprises:

a supply catcher unit configured to transport the cuvette arranged at the predetermined position to a dispensing table; and a cuvette moving unit configured to move the cuvette between the dispensing table and a second optical information acquiring unit having the optical detector.

18. The specimen analyzer according to claim 1, wherein the arranging section further comprises a table having a cutout, and the transportation rail is configured to arrange the cuvette at the cutout as the predetermined position.

* * * * *